(12) United States Patent
Cowe et al.

(10) Patent No.: US 10,722,654 B2
(45) Date of Patent: Jul. 28, 2020

(54) INJECTION DEVICE

(71) Applicant: Owen Mumford Limited, Oxford (GB)

(72) Inventors: Toby Cowe, Oxford (GB); Cosimo Santella, Cambridge (GB); Colin Plimmer, Cambridge (GB)

(73) Assignee: Owen Mumford Limited, Oxford (GB)

( * ) Notice: Subject to any disclaimer, the term of this patent is extended or adjusted under 35 U.S.C. 154(b) by 775 days.

(21) Appl. No.: 15/119,479

(22) PCT Filed: Feb. 18, 2015

(86) PCT No.: PCT/GB2015/050466
§ 371 (c)(1),
(2) Date: Aug. 17, 2016

(87) PCT Pub. No.: WO2015/124923
PCT Pub. Date: Aug. 27, 2015

(65) Prior Publication Data
US 2017/0007765 A1 Jan. 12, 2017

(30) Foreign Application Priority Data
Feb. 18, 2014 (GB) .................................. 1402826

(51) Int. Cl.
*A61M 5/24* (2006.01)
*A61M 5/315* (2006.01)
(Continued)

(52) U.S. Cl.
CPC .............. *A61M 5/24* (2013.01); *A61M 5/172* (2013.01); *A61M 5/2033* (2013.01);
(Continued)

(58) Field of Classification Search
CPC .......... A61M 5/172; A61M 2205/8206; A61M 5/24; A61M 5/3156
See application file for complete search history.

(56) References Cited

U.S. PATENT DOCUMENTS 4,345,483 A * 8/1982 Paletta ................. A61M 5/172
422/562
5,300,030 A 4/1994 Crossman et al.
(Continued)

FOREIGN PATENT DOCUMENTS

CN 1406641 A 4/2003
CN 200948276 Y 9/2007
(Continued)

OTHER PUBLICATIONS

International Search Report and Written Opinion of the International Searching Authority issued in PCT Application No. PCT/GB2015/050466, dated Jun. 2, 2015, 11 pages.
(Continued)

*Primary Examiner* — Nathan R Price
*Assistant Examiner* — Melissa A Snyder
(74) *Attorney, Agent, or Firm* — Quarles & Brady LLP

(57) ABSTRACT

An injection device (1) includes a housing (20) for receiving a cartridge (30) of medicament in use; a drive element (12), moveable from a first position to a second position to expel a dose from said cartridge, and wherein the drive element comprises an electrically-operated indicator module (40) for generating an indication corresponding to the stage of use of the device. The indicator module (40) may be contained within the drive element, for example within an interior of the drive element and may include an audible indicator such as e.g. a sounder or loudspeaker, and a visual indicator such as e.g. one or more LEDs arranged to provide e.g. colour-coded signals.

30 Claims, 13 Drawing Sheets

(51) Int. Cl.
  *A61M 5/32* (2006.01)
  *A61M 5/172* (2006.01)
  *A61M 5/20* (2006.01)

(52) U.S. Cl.
  CPC ........ *A61M 5/3157* (2013.01); *A61M 5/3202* (2013.01); *A61M 5/3243* (2013.01); *A61M 2005/202* (2013.01); *A61M 2005/206* (2013.01); *A61M 2205/50* (2013.01); *A61M 2205/581* (2013.01); *A61M 2205/583* (2013.01); *A61M 2205/8206* (2013.01)

(56) References Cited

U.S. PATENT DOCUMENTS

| | | | |
|---|---|---|---|
| 6,620,133 | B1 | 9/2003 | Steck |
| 9,943,651 | B2 * | 4/2018 | Deutsch .......... A61M 25/10182 |
| 2001/0034502 | A1 * | 10/2001 | Moberg .............. A61M 5/1456 604/154 |
| 2007/0021715 | A1 | 1/2007 | Kohlbrenner et al. |
| 2008/0312604 | A1 | 12/2008 | Boesen |
| 2009/0156990 | A1 * | 6/2009 | Wenger ............. A61M 5/14244 604/67 |
| 2011/0238017 | A1 * | 9/2011 | Watanabe ......... A61M 5/14546 604/189 |
| 2013/0131589 | A1 * | 5/2013 | Mudd ..................... A61M 5/19 604/82 |
| 2013/0131602 | A1 * | 5/2013 | Kemp ................ A61M 5/2033 604/197 |
| 2014/0039396 | A1 * | 2/2014 | Geipel ............. A61M 5/14216 604/152 |

FOREIGN PATENT DOCUMENTS

| | | |
|---|---|---|
| CN | 101516421 A | 8/2009 |
| CN | 201375731 Y | 1/2010 |
| CN | 101862489 A | 10/2010 |
| CN | 102076332 A | 5/2011 |
| CN | 102202711 A | 9/2011 |
| CN | 102580181 A | 7/2012 |
| EP | 2716313 A1 | 4/2014 |
| EP | 2716318 A1 | 4/2014 |
| EP | 2958610 B1 | 11/2016 |
| WO | 2008/037801 A1 | 4/2008 |
| WO | 2010/052275 A2 | 5/2010 |
| WO | 2011120587 A1 | 10/2011 |
| WO | 2012/160164 A1 | 11/2012 |
| WO | 2014128155 A1 | 8/2014 |

OTHER PUBLICATIONS

Search Report issued in United Kingdom Patent Application No. 1402826.0, searched Sep. 15, 2014, 2 pages.
Communication issued pursuant to Article 94(3) EPC in corresponding European Patent Application No. 15709544.9, dated Jan. 18, 2019, 4 pages.
First Office Action issued in corresponding Chinese Patent Application No. 201580009241.5, dated Oct. 9, 2018, 9 pages.
Third Office Action issued in corresponding Chinese Patent Application No. CN20158009241.5, dated May 24, 2019, 8 pages. (English translation not included).

* cited by examiner

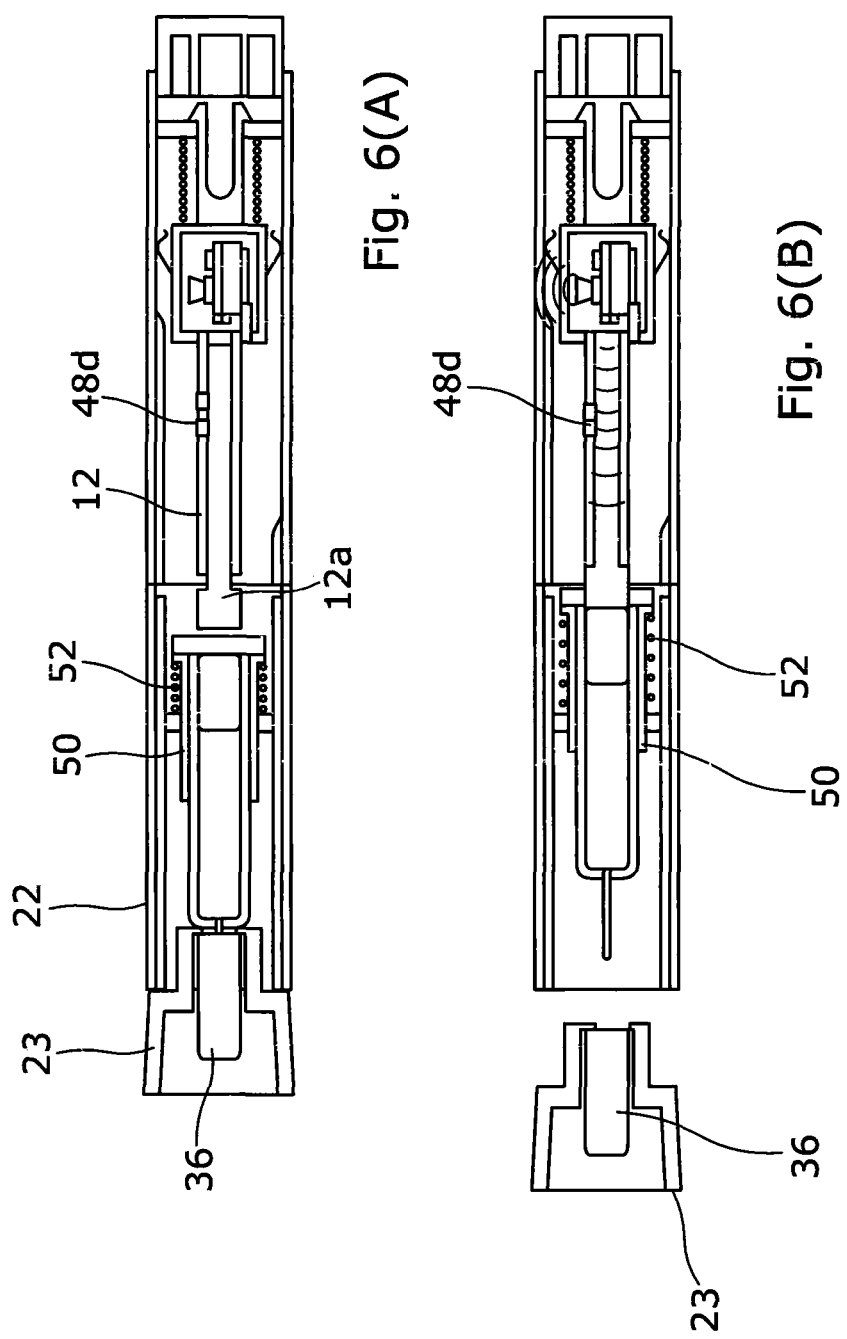

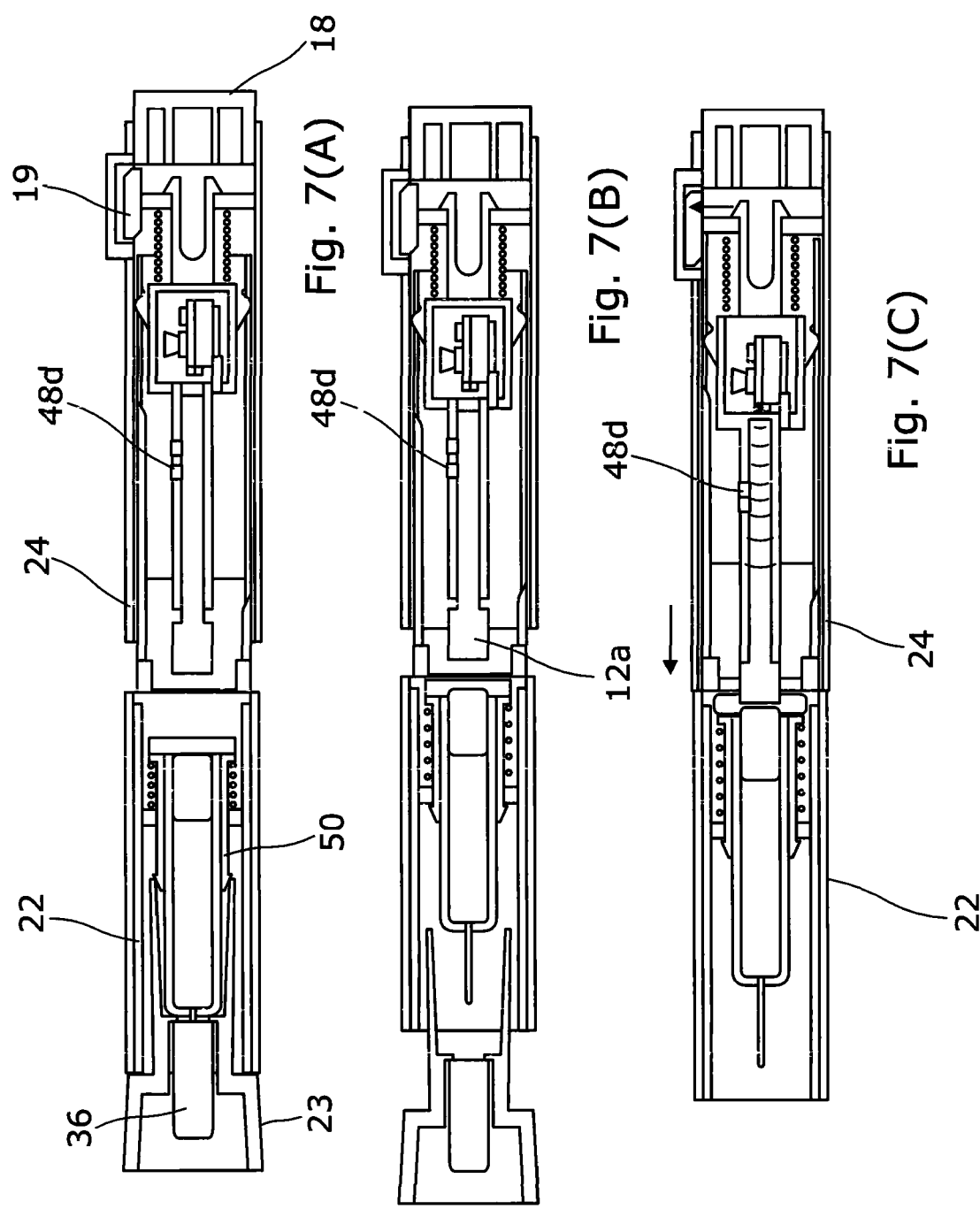

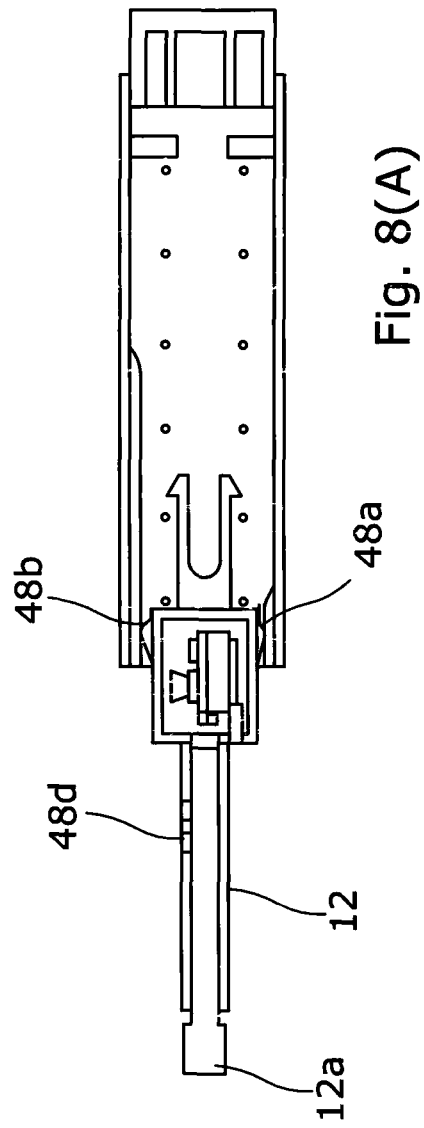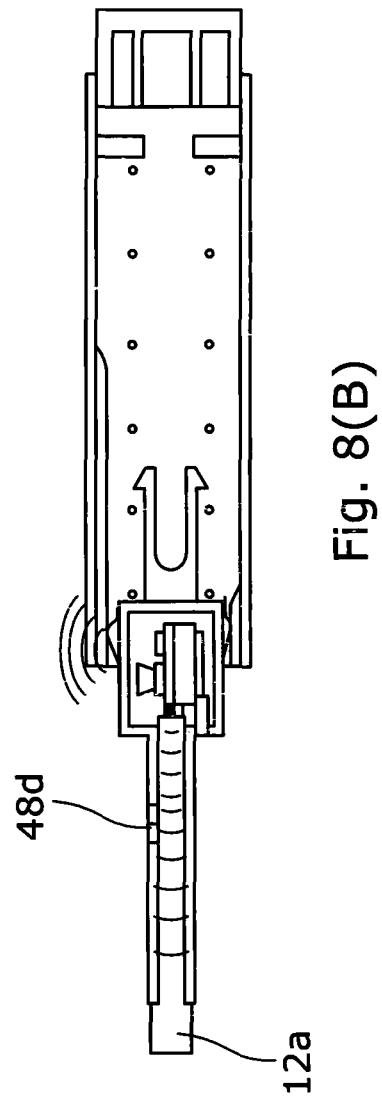

INJECTION DEVICE

CROSS-REFERENCE TO RELATED APPLICATIONS

This application represents the U.S. National Stage of International Application No. PCT/GB2015/050466 filed Feb. 18, 2015, which is based on, claims priority to, and incorporates herein by reference in its entirety, British Patent Application Serial No. GB 1402826.0, filed Feb. 18, 2014, and entitled, "Injection Device."

FIELD OF INVENTION

This invention relates to injection devices, and in particular, but not exclusively, to reusable auto-injection devices comprising a housing into which a disposable syringe or cartridge may be inserted to effect the injection and then removed and replaced as required for the next injection.

BACKGROUND OF INVENTION

Injection devices, such as the Owen Mumford Autopen®, are commonly used by patients to self-administer injections of medicament. Such devices are typically provided in a pen-like body which contains a cartridge of medicament (it will be appreciated that the cartridge may, for example, comprise a syringe and may be received within or defined by the injector housing depending on the particular device configuration; as such references herein to a "cartridge" will be interpreted accordingly). The injection device generally comprises a delivery mechanism which is arranged to dispense the medicament via a needle in response to a user pressing a button or trigger. Depending upon the type of device and or medicament to be delivered the injection device may be arranged to deliver the entire contents of the cartridge or a selected dose therefrom (and in the latter case the injector may also include a dose selection device). In some injection devices the delivery mechanism may also be arranged to move the needle between a retracted and delivery position and, in doing so, may automatically pierce the skin of the user prior to the dispensing of the medicament.

It is a common requirement that injection devices signal to the user when the injection is complete. The term 'injection complete' is used to refer to a condition in which a satisfactory delivery of the drug has been achieved. Such an indication may be one or more of a visual, audible or tactile indication.

One such arrangement has been provided in the applicant's earlier International Patent Application WO2009/141650 in which an injection device is provided with a magnetically-operated indicator for generating an injection complete indication.

A further injection device is disclosed in WO2006/134153, in which an injection pen is provided with a plurality of sensors that sense when a user is taking a specific action with the device and a sound generator to generate a signal corresponding to the action being taken.

STATEMENTS OF INVENTION

In one aspect this invention provides an injection device including: a housing for receiving a cartridge of medicament in use; a drive element, moveable from a first position to a second position to expel a dose from said cartridge, and wherein the drive element comprises an electrically-operated indicator module for generating an indication corresponding to the stage of use of the device.

The indicator module may be disposed on the drive element. The indicator module may be contained within the drive element, for example within an interior of the drive element. The drive element may comprise a hollow body. All of the electrically conductive components may, for example, be contained within an interior of the drive element. Advantageously, therefore embodiments of the invention may provide an arrangement in which the indicator module is self-contained and does not require any separate electrical components to be provided on the housing.

Typically, the drive element may comprise a plunger which is arranged to engage a piston within the cartridge. The drive element may be part of a delivery mechanism for dispensing medicament. The delivery mechanism may further comprise an activation trigger and a stored energy device which is released to drive the element forward into the cartridge. The stored energy device may for example be compressed gas, an electrical actuator, a torsion spring, a constant force spring, or a compression spring.

The indicator module may comprise a battery (which may comprise a plurality of batteries). The battery(s) may be replaceable, for example, the drive element may comprise separable body portions to allow access to the battery. The indicator module may comprise a controller, which may for example be a microprocessor. The controller may be part of a PCB.

The indicator module may typically comprise an indication device. The indication device may comprise a transducer for converting an electrical signal into one or more of an acoustic, visual or tactile indication signal. For example, the indication device may comprise a sound emitter. The indication device may comprise a loudspeaker. Additionally, or alternatively the indication device may comprise at least one illumination device (which may for example be an LED).

The drive element may further comprise a translucent body extending along at least a portion of the drive element. The translucent body may be arranged to transmit indications from the illumination device.

This arrangement may provide an advantageous indication arrangement in its own right. Thus, in a further aspect of the invention there is provided an injection device comprising: a housing for receiving a cartridge of medicament in use; a drive element moveable from a first position to a second position to expel a dose from said cartridge; and an indicator comprising an illumination device for generating an indication corresponding to the stage of use of the device; and wherein the drive element comprises a translucent body extending along at least a portion of its length and arranged to transmit indications from the illumination device.

It will be appreciated that translucent body may be substantially transparent. The translucent body may comprise a transparent plastic body. For example, the translucent body may comprise a polished polycarbonate section of the drive element. The translucent body may, for example, comprise a light pipe which transmits light from the illumination device along its axial length. The translucent body may be hollow and the illumination device may be disposed within or aligned with the interior of the body. The translucent body may comprise the plunger of the drive element (and may extend along a substantial axial length of the injector device).

It is known for injection devices to be provided with a viewing window in the housing which is substantially aligned with the cartridge (such that the cartridge and medicament therein may be viewed). As such, the translucent body may be arranged to transmit illumination signals from the illumination device to the viewing window.

Additionally or alternatively, other cut-outs or windows may be provided in the housing for viewing of the illumination signals.

The drive element may further comprise at least one switch. The housing may comprise at least one associated trigger point arranged to engage the switch when the switch is in axial alignment with the trigger point. This arrangement advantageously ensures that all of the electrical components are associated with the drive element whilst the housing may remain relatively simple. Further, this may also be advantageous for assembly of the injection device since the electronic components may all be integrated into a single modular component. The trigger point may be radially inwardly extending. The trigger point may comprise an axially extending rib. By providing an axially extending trigger point the switch may be triggered upon initial alignment between the switch and the trigger point and may remain in contact for a desired range of the motion of the drive element relative to the housing.

In some embodiments the drive element may comprise a single switch which is triggered by multiple trigger points at separate axial locations (which would for example each relate to different stages of the operation of the device).

In a further embodiment the drive element may comprise a plurality of switches and the housing comprises a plurality of associated trigger points. Each trigger point may be disposed at a different axial location. For example the rearward most point of each trigger may be at a different axial location. Thus, the switches may be arranged to be triggered in a chosen sequence during movement of the drive member relative to the housing (for example during the activation of the device). Each of the plurality of switches and associated trigger points may be radially distributed about the housing and drive element.

The controller of the indication module may be arranged to receive a plurality of signals from a plurality of switches and may apply a predetermined logic to the inputs to trigger an appropriate indication.

The, or each, switch could comprise an electrical contact which is closed by contacting a conductive member on the housing. Alternatively, the, or each, switch may comprise an outwardly directed contact member which is deflected inwardly by the associated trigger point. The contact member may be outwardly biased. The contact member may comprise a spring contact. Alternative switch arrangements may also be used for example a micro switch or a membrane switch.

The housing may comprise a shroud assembly arranged to shroud the needle of the cartridge after use (and such arrangements will be known to those skilled in the art). The drive element may be provided with a switch which is arranged to engage a portion of the shroud when the drive element is in a forward position. Thus, the microprocessor may be able to determine the position of the shroud after the drive element moves to the forward position (i.e. after delivery of the medicament).

The drive element further comprises a compression switch, which is activated by compressive load on the drive element. The compression switch may be arranged to react to compressive load on the drive element in the axial direction. For example, the drive element may comprise a forwardly biased portion and the compression switch may comprise a switch against which the forward biased portion may be moved into contact against the bias. The forwardly biased portion may for example be the plunger of the drive element (which may for example be a light pipe as discussed above). The compression switch may be provided on a backstop for the forwardly biased portion.

The device further comprises a removable needle shield (which as in known devices may be arranged to remove a protective/sterile cover from a needle in preparation for use). The needle shield may be a rigid needle shield. The removal of the needle shield may be arranged to compress the drive element. For example, the cartridge may be held against a rearward biasing force by the needle shield and moves rearwardly relative to the drive element upon removal of the needle shield.

A cap may be removably connected to the forward end of the housing. The cap may engage the needle shield and be arranged to remove the needle shield upon removal of the cap from the housing. Thus, the cap may couple the housing and the needle shield prior to removal (and may, therefore, hold cartridge against the rearward biasing). The removal of the shield by the cap may allow release the cartridge for rearward movement relative to the drive member.

The housing may comprise front and rear portions which are relatively axially slidable. For example, it is known to provide an arrangement in which the delivery mechanism cannot be fired until front and rear housing portions are compressed together when the device is pressed against an injection site (for example, the device may include an interlock in which a physical block prevents triggering of the delivery mechanism). The axial compression of the housing portions may be arranged to compress the drive element.

The compression of the drive element required to activate the compression switch may require both the removal of the needle shield and the axial compression of the housing portions. This advantageously, ensures that the switch is only activated when the injection device is in a state in which it is ready to fire.

The housing may comprise front and rear separable portions to allow removal and replacement of the cartridge. The front may be arranged to receive the cartridge. The rear portion may contain the delivery mechanism. Separation of the housing portions the drive member is moved to a position in which the indicator is deactivated. For example, the, or each, trigger point may end at a point which is rearward spaced from the forward end of the rear housing and the switches may move beyond the trigger points upon separation of the housing.

In the separated position a switch on the drive element may be used to test the battery power status of the indicator. For example, the controller may be arranged to respond to an activation of one of the switches (for example the compression switch on the drive element) by providing a battery status indication. This may for example provide the user with a convenient means of testing the battery by simply pressing the drive member during reloading of the cartridge.

The injector device may further comprise a dose counter. For example the controller may be arranged to count doses being administered based upon the indicator signals. The device may comprise an additional display, for example on the housing, for displaying dose count indications.

The indicator is arranged to provide a plurality of different colour visual illuminations. For example the indicator may include a plurality of different coloured illumination devices (for example multiple coloured LEDS). The illumination devices may be used in combination to provide additional colour illuminations (for example by simultaneous illumination of the translucent member in some statuses).

The indication corresponding to the stage of use of the device includes one or more of: a ready to fire signal; an injection initiation signal; an injection complete signal; a device safe signal and an alarm signal. The injection initiation signal may indicate that the drive element has been released. The injection complete signal may indicate that the dose of medicament has been fully dispensed (and may be triggered only after a pre-set delay from the completion of the drive element movement). The alarm state may, for example, be triggered if an injection is not complete within a set time period after release of the drive element. The safe signal may be indicated when the injector device has returned to a shrouded or shielded state after completion of an injection.

According to a further aspect of the invention there is provided a drive element for an injection device comprising an electrically-operated indicator module for generating an indication corresponding to the stage of use of the device. The drive element may be arranged to be moveably mounted within a substantially standard injection device. The indicator module may be contained with an interior of the drive element. The drive element may comprise one or more of the preferred features described above with reference to the injection device. All of the electrically conductive components may, for example, be contained within an interior of the drive element.

In some embodiments the at least one switch and the housing may include at least one feature which is arranged to trigger the switch in a pre-determined pattern or periodic manner during axial movement of the drive element. The controller may monitor the resulting repeated triggering of the switch to determine the position and or movement of the drive element during activation of the injection device.

Accordingly, a further aspect of the invention comprises an injection device comprising a housing for receiving a cartridge of medicament in use; a drive element, moveable from a first position to a second position to expel a dose from said cartridge, and wherein the injection device comprises an electrically-operated indicator module for generating an indication corresponding to the stage of use of the device, the injection module comprising a switch which is triggered by contact with a complementary feature when axial movement of the drive element relative to the housing aligns the feature and switch and wherein the feature is profiled along its axial length such that the switch is repeatedly activated during axial movement of the drive element.

The feature may comprise a sequence of radial projections at spaced apart axial locations. The feature may have a periodic profile in the axial direction. For example, the feature may comprise a toothed track.

The switch may be provided on the drive element and the feature may be formed on an inner surface of the housing. For example, the feature may comprise an axially extending rib. As such, it will be appreciated that the injection device may incorporate one or more of the preferred features of the injection device and/or drive member described in conjuction with the other aspects of the invention above.

The injection device may further comprise a controller, the controller being arranged to monitor the repeatedly activation of the switch to measure/determine the movement and/or position of the drive element.

Whilst the invention has been described above, it extends to any inventive combination of feature set out above or in the following description and/or drawings.

BRIEF DESCRIPTION OF DRAWINGS

Preferred embodiments of the invention will now be described in detail, by way of example only, and with reference to the accompanying drawings in which:

FIG. 6 is a schematic cross-section showing an injection device according to a further embodiment of the invention including an additional cap feature;

FIG. 7 is a schematic cross-section showing an injection device according to a further embodiment of the invention including an interlock feature;

FIG. 8 is a schematic cross-section illustrating a battery check function;

DETAILED DESCRIPTION OF THE EMBODIMENTS

Front as used herein will be understood to refer to the end of the injection device assembly (or components thereof) which, in use, are closest to the delivery needle end of the injection device (i.e. the end which is intended to be proximal to the skin). Rear as used herein will be understood to refer to the end of the injection device assembly (or components thereof) which, in use, are furthest from the delivery needle end of the pen injection device (i.e. the end which is intended to face away from the skin). Likewise, forward and rearward will be understood to refer to the directions orientated towards the front and rear of the injection device assembly.

Figure 1:
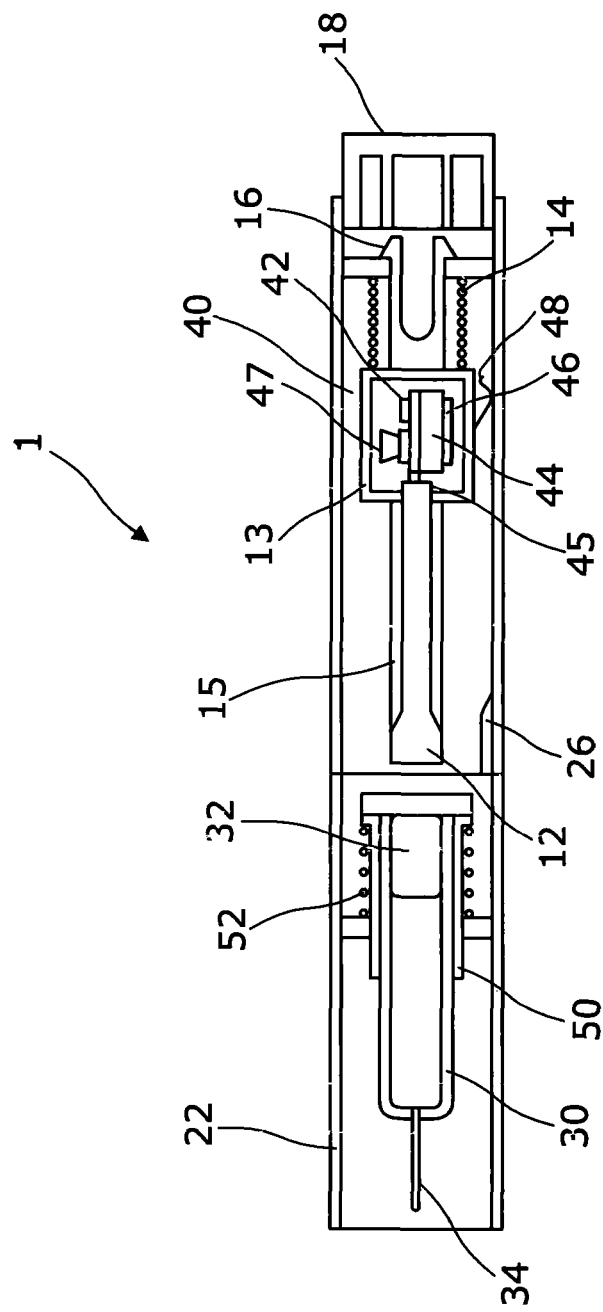
FIG. 1 is a schematic cross-section of an injection device according to an embodiment of the invention.

As shown in FIG. 1, embodiments of the invention comprise an injection device (1) comprising a housing (20) formed of a forward housing portion (22) and a rearward housing portion (24). The housing portions may be removably connected to one another, for example by screw threaded portions or the like. Within the forward housing portion (22) there is provided a cartridge (30) containing a medicament to be delivered in use. The cartridge comprises a piston (32) at its rearward end which may be urged forward relative to the body of the cartridge to expel the medicament therefrom. A needle (34) is provided at the forward end of the cartridge and may, for example, be part of a removable needle assembly. The rear housing portion (24) contains a delivery mechanism (10) which the skilled person will appreciate may use any one of a number of known arrangements which is suitable for moving a drive element (12) between a rearward position and a forward position so as to drivingly engage the piston (32) within the syringe (30).

In the illustrated embodiment, the delivery mechanism (10) comprises an energy storage device in the form of a compression spring (14) and a latch (16) which is arranged to hold the drive element (12) in a rearward position against the forward bias of the spring (14). A trigger, which may be a simple button (18), is provided at the rear of the housing

(20) and may be depressed in use to release the latch (16) and enable the spring (14) to drive the drive element forwards.

The illustrated embodiment is also an arrangement in which the cartridge (30) is initially biased rearwardly such that the needle (34) is fully contained within the forward housing (22). As such, the injection device (1) further comprises a cartridge carrier (50) which is biased towards a rearward position by a biasing spring (52). As will be understood by those skilled in the art, upon firing of the delivery mechanism (10) the drive element (12) will engage the piston (32) and due to the generally incompressible nature of the medicament within the cartridge (30) will first act to drive the cartridge (30) forwards such that the needle (34) may project beyond the end of housing (22) and penetrate the skin at the injection site. Once the cartridge (30) has reached its forward position the carrier (50) will reach a physical stop and further forward movement of the drive element (12) will move the piston (32) relative to the cartridge (30) to dispense the medicament via the needle (34). It will be appreciated that other arrangements are possible in which the cartridge is fixed and insertion of the needle is manually achieved and embodiments of the invention may be equally applicable to such injection devices.

In accordance with embodiments of the invention the injection device (1) further comprises an electrically-operated indicator module (40) which is contained within a rearward portion of the drive element (12). The drive element (12) may be provided with a portion (13) with locally increased radial dimensions so as to accommodate the indication module (40). The module includes a microprocessor (42), a printed circuit board (44), a battery (46), an LED indicator (45), a loudspeaker (47) and a switch (48) which includes an outwardly biased contact. Conveniently the module (40) is entirely contained within the drive element and does not require any additional components to be formed in the housing (20). This, for example, may simplify the integration of the indicator module into an otherwise standard injection device and/or may help simplify manufacture and assembly of the injection device. The only adaptation to the housing (20) is the provision of a trigger point (26) which is arranged to engage the switch (48) during operation.

The trigger point comprises an axially extending rib which projects radially inwardly into the space within the rear portion of the housing (24) including a ramp surface at its rearward most end and. The axial position of the trigger point (26) is chosen such that the switch (48) will be axially aligned with the trigger point (26) at the point in the firing sequence of the device (1) when the switch (48) is to be closed. Whilst in the drawings the trigger point (26) is shown as extending fully to the forward most point of the rear portion of the housing (24) it may be desirable for the rib (or each) to stop slightly short of the front. This may allow the drive element (12) a small amount of over travel (for example when the housing portions are separated or when no cartridge is present) in the forward direction which disengages the switch (48) or switches of the indicator module. This may, for example provide an auto power-off function to save unnecessary battery use.

In order to transmit the visual indications from the indication module (40) the forward portion (15) of the drive element (12) may be formed from a translucent material, for example transparent polished polycarbonate and the illumination device (45) may be aligned with the interior of the translucent section (15). This may, for example be useful if the injector device includes a viewing window (not shown) in the forward portion of the housing (22).

Figure 2A:
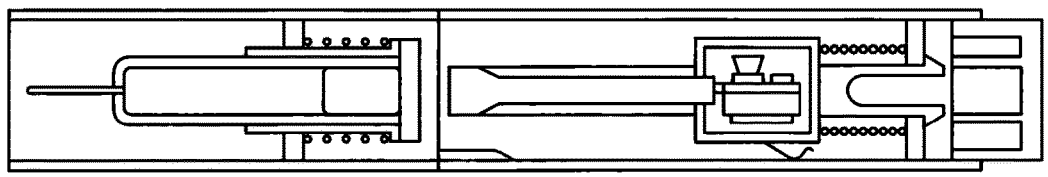
FIG. 2 is a schematic cross-sectional showing the operating sequence of the embodiment of FIG. 1.
Figure 2B:
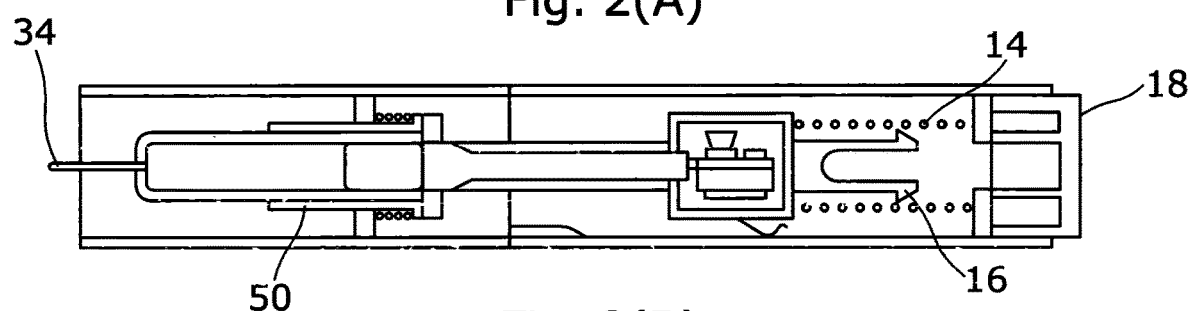
Figure 2C:
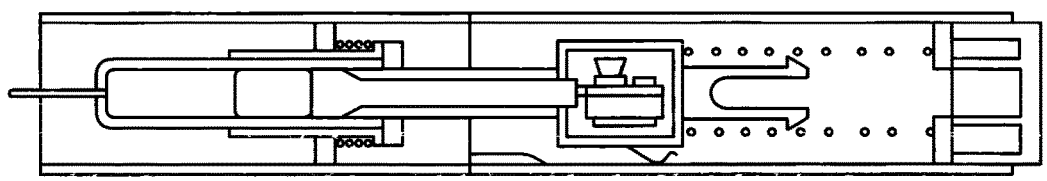

Operation of the embodiment of FIG. 1 is illustrated in the sequence of FIGS. 2a to 2d. FIG. 2a shows the initial, pre-firing, configuration of the injector device (1) (and is substantially identical to FIG. 1). The user activates the device by depressing the trigger button (18) as shown in FIG. 2b. The trigger (18) releases the latch (16) at the rear of the delivery mechanism (10) such that the drive spring (14) may urge the drive element (12) forwards. As mentioned above, initial engagement of the piston (32) by the drive element (12) compresses the biasing spring (52) and moves the cartridge (30) into a forward position such that the needle (34) may extend beyond the housing (20) and penetrate the skin. Once the syringe (30) reaches it forwardmost position continued movement of the drive element (12) moves the piston (32) forwardly within the cartridge (30) such that delivery of the dose of medicament is begun as shown in FIG. 2c.

Figure 2D:
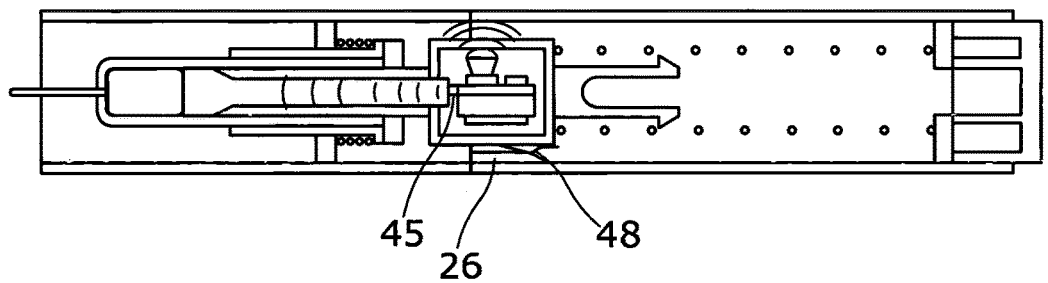

When the piston (32) has been fully driven forwards the entire dose of medicament from the syringe (30) has been delivered as shown in FIG. 2d. Slightly before this point the switch (48) has moved into alignment with the trigger point (26) and has been closed by travelling up the rearward ramp surface onto the rib of the trigger point. The microprocessor (42) receives a signal from the switch (48) and, after a predefined delay has lapsed, triggers both an audible indication from the loudspeaker (47) and a visual indication from the LED (45) which is transmitted and/or amplified by the translucent portion (15) of the drive member (12). Typically, a short delay may be built into the indication between the switch (48) being triggered to indicate that the piston (32) has reached its forward most position and the provision of a signal to the user so that the dose is completed, and to ensure that the user does not prematurely withdraw the needle (34).

As mentioned above, it may be noted that the switch position of the "injection complete" indication (which is defined by the position of the trigger point (26)) is slightly before the end of the stroke of the drive element (12). This is provided by positioning the trigger point a few millimetres rewards of the true end of dose position of the switch (48) on the drive element (12). This allows for for variations in tolerances of cartridge and/or device. For example, the trigger point should be chosen such that the shortest cartridge/device tolerance stack will close the switch (since then all variations will). This inevitably leads to some lag between the switch (48) being closed by the trigger point (26), and the piston (32) actually reaching the end of its movement. The delay in the microprocessor program and the fact that the switch contact does not arrest forward travel ensures that the indication will occur when the longest syringes are fully evacuated, even though the trigger point is designed to work with the shortest syringes.

Figure 3:
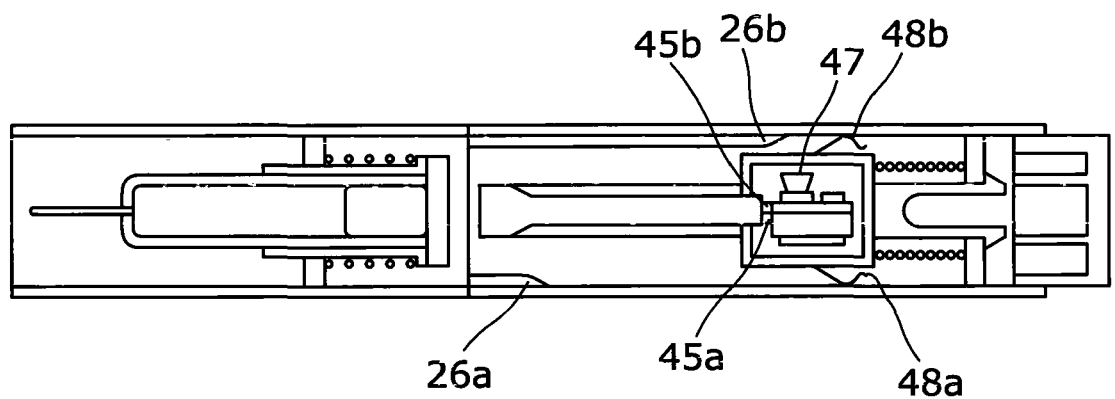
FIG. 3 is a schematic cross-section of an injection device according to a further embodiment of the invention.
Figure 9:
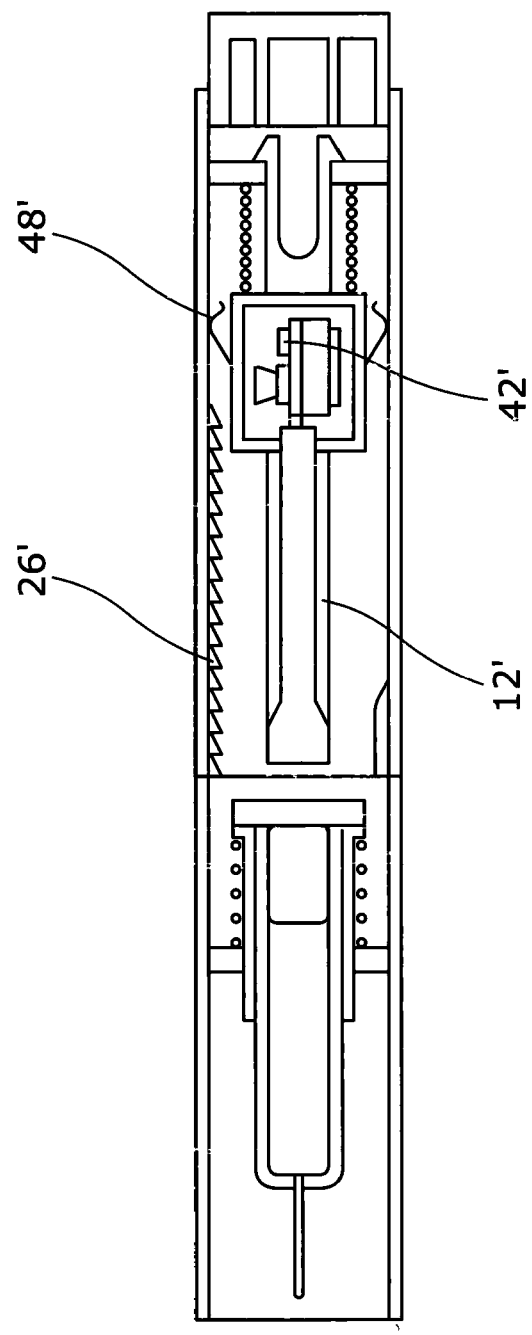
FIG. 9 is a schematic cross-section showing a further embodiment including a periodic switch trigger.

FIG. 3 illustrates a second embodiment of the invention in which the injector device (1') is substantially identical to the injector of the first embodiment but includes a plurality of switches (48a and 48b). Each switch is associated with a separate trigger point (26a, 26b). The switches (48a and 48b) may be provided at different circumferential positions on the drive element (12) with the trigger points (26a and 26b) provided at aligned positions on the inner circumference of the rear housing (24). It may be noted that the trigger points (26a and 26b) are each arranged to start at a different rearward axial position but both extend forwardly to the forward most end of the rearward portion of the housing (24). This arrangement ensures that each trigger point closes its respective switch (48) when the drive element (12) reaches the desired point in its forward movement and remains closed until the movement of the delivery mechanism (10) is complete. It will, of course, be appreciated that alternatively the trigger points (26) could only close the switch (48) for a short period of the movement depending on the particular control and signalling arrangements which are programmed into the microprocessor (42). In another alternative which is illustrated in FIG. 9, the trigger point (26) could be arranged to open and close the switch multiple times along the delivery stroke (for example in a predetermined pattern or periodic manner). This repeated triggering of the switch (48) could be used by the microprocessor (42) to determine and/or monitor the progress of the drive element (12) during movement. For example, if a normal time period between on/off cycling of the switch (48) was exceeded the forward movement of the drive element (12) may be assumed to have ceased.

In addition to the multiple trigger points the embodiment of FIG. 3 differs from the embodiment of FIG. 1 in that the indication module (40) is provided with two indication devices (45a and 45b) in the form of two different coloured LEDs which are both associated with the interior of the translucent portion (15) of the drive element (12). The actuation sequence of the second embodiment is substantially the same as the actuation sequence of the first embodiment but as shown in FIG. 4 includes additional indications. For example, the additional switch (48b) and trigger point (26b) may be arranged such that they come into alignment as the cartridge (30) reaches its forward most position and may be used to trigger an "injection initiated" signal which indicates to the user that delivery of the medicament has commenced.

Figure 4A:
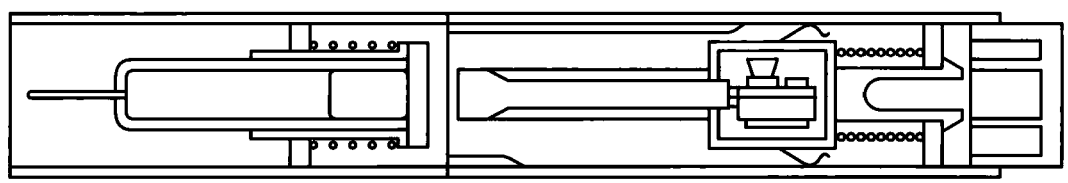
FIG. 4 is a schematic cross-sectional showing the operating sequence of the embodiment of FIG. 3.
Figure 4B:
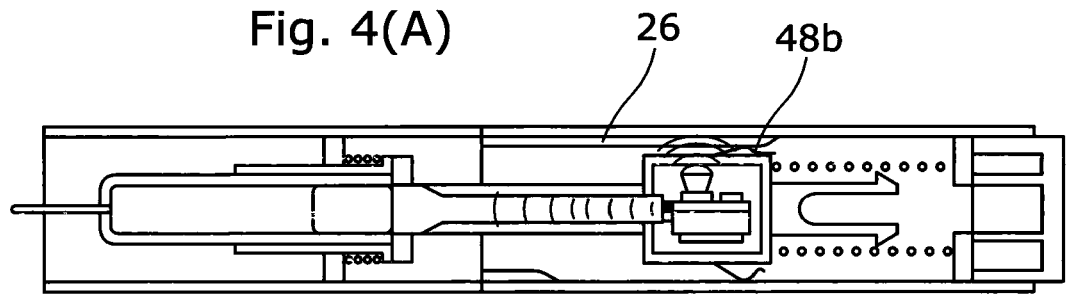
Figure 4C:
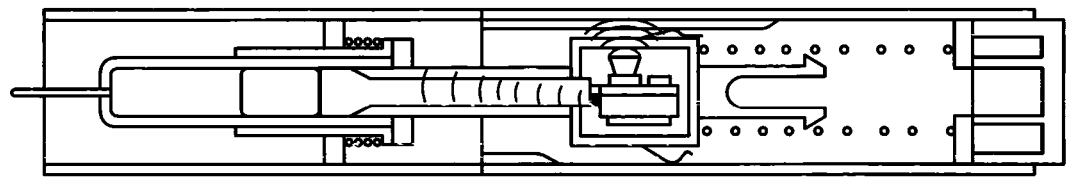
Figure 4D:
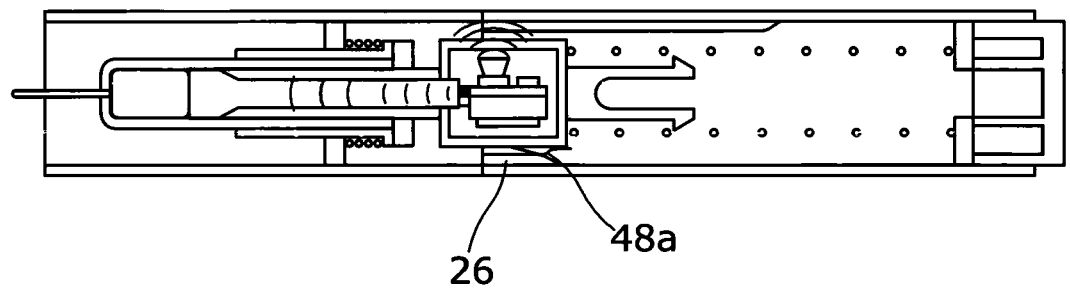

One additional advantage of providing a switch to detect the start of delivery is that the microprocessor may further be arranged to provide an alarm in the event that the injection complete signal (of FIG. 4d) is not triggered within a normal time period after the initiation switch (48b) is triggered. Thus, as shown in FIG. 4c the second LED may for example be used to provide a red visual indication and the loudspeaker used to provide an audible indication substantially different from the injection complete indication to inform the user that the injection is not progressing as expected. For example, the alarm signal could be triggered if the injection is not complete within 10 to 15 seconds of the first switch (48b) being triggered.

FIG. 5 illustrates a third embodiment in which the injection device further includes a releasable shroud (28) which is arranged to extend forwardly of the front portion (22) of the housing (20) after completion of the injection so as to protect the needle (34) and prevent unwanted needle stick injuries. Such shroud arrangements are well-known in the art. In this embodiment the indication module (40) includes a further switch (48c) which is arranged to engage or abut a rearward portion of the needle shroud (28) when the drive element (12) is in its forward most position. As with switches 48a and 48b, switch 48c may be designed such that travel is not arrested once this switch is triggered.

Figure 5A:
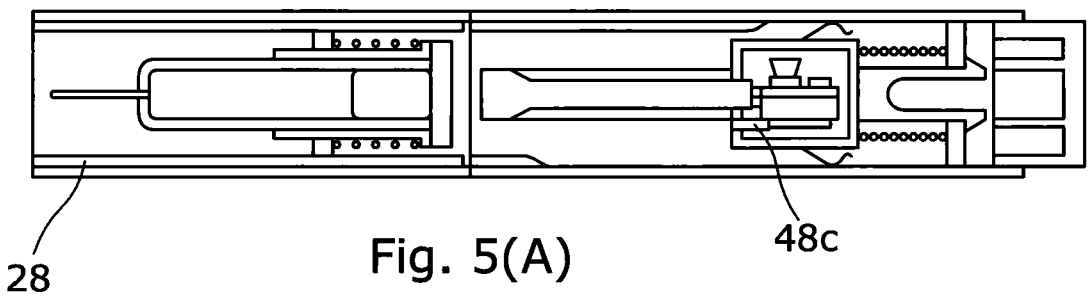
FIG. 5 is a schematic cross-section showing the sequence of operation of an injection device according to a further embodiment of the invention.
Figure 5B:
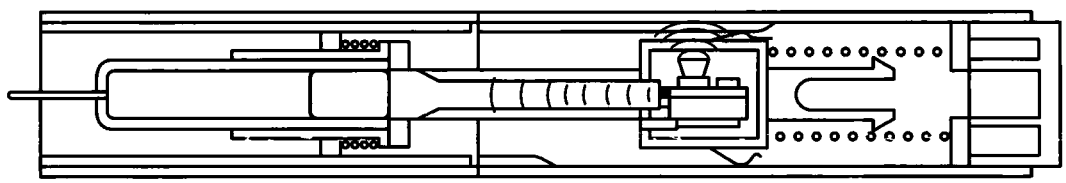
Figure 5C:
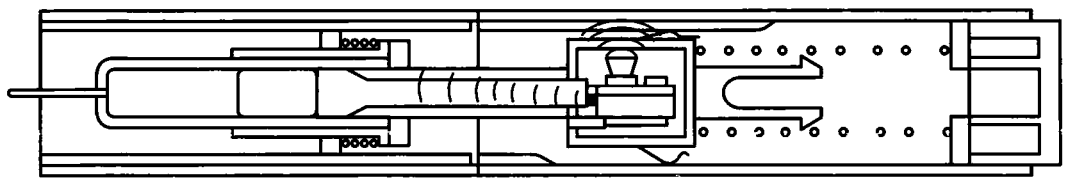
Figure 5D:
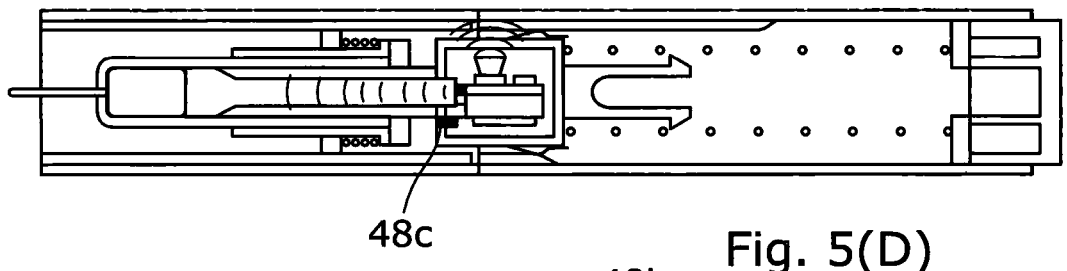
Figure 5E:
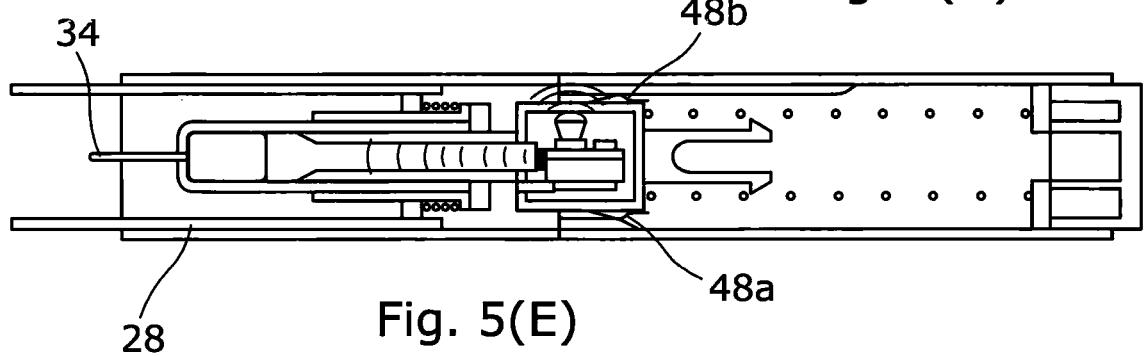

The general sequence of actuation of this third embodiment is substantially the same as the second embodiment including an injection initiation signal (FIG. 5b), an alarm signal (FIG. 5c) and an injection complete signal (FIG. 5d). However, in this embodiment in the injection complete position the additional switch (48c) is depressed by engagement with a portion of the needle shroud (28) and when the user removes the injection device from the injection site the shroud (28) is arranged to move forwardly as shown in FIG. 5e. Forward movement of the shroud releases the switch (48c) and the microprocessor is able to identify this release since, in contrast to the status of FIG. 5d, now only switches 48a and 48b are active. The microprocessor then provides a separate indication to inform the user that the device is now safe. Conveniently the safe indication may be provided by illuminating both of the LEDs (45a and 45b) which are jointly transmitted through the translucent portion (15) of the drive element (12) and provide a third colour of visual indication (for example purple when the LEDs are blue and red).

FIG. 6 illustrates a further embodiment of the invention in which the cartridge (30) is provided with a needle shield (36) which protects and maintains sterility of the needle (34) prior to use. The forward housing (22) is provided with a cap (23) which engages the needle shield (36) and which is arranged to remove the needle shield (36) upon disconnection of the cap (23) from the body (22) (as shown in FIG. 6b). As best seen in FIG. 6a the coupling between the cap (23) and needle shield (36) in the initial position is arranged to hold the cartridge (30) in a forward position such that the cartridge (50) is compressed against the rearward biasing spring (52). Upon removal of the cap (23) and needle shield (36) the carrier (50) and cartridge (30) move rearwardly to the initial position shown in the previous embodiments. The indicator module includes a further switch (48d) which is arranged to be activated by a compressive load on the drive element (12) (and is referred to herein as a 'compression switch'). In the illustrated embodiment, for example, the drive element (12) may include an inner member (12a) which is arranged such that it may have a small degree of axial movement relative to the main part of the drive element. Upon removal of the cap (23) and needle shield (36) the cartridge (30) is pressed rearwardly against the drive element (12) and places a compressive load on the drive element. Thus, the slideable member (12a) may be moved rearwardly and may close the contacts of the switch (48d). The indicator module may respond to this activation by providing a ready signal (for example a simple flash or beep of the loudspeaker and/or LED) to indicate to the user that the device is ready for use.

FIG. 7 shows a further embodiment in which in addition to the cap and needle shield of FIG. 6 the injector includes an arrangement in which the front (22) and rear (24) housing portions must be slid axially together prior to actuation of the delivery mechanism. This sliding action between the housing portion may occur when the device is pressed against an injection site and may be arranged to release a physical block (19) which otherwise prevents firing of the delivery arrangement by the trigger (18) (such devices are known in the art and are generally referred to as an "interlock" arrangement, the interlock may for example require a rotary or sliding action to disengage).

As in the embodiment of FIG. 6 this embodiment is initially provided with the cartridge biased forwardly by the cap (23) engaging the removable needle shield (36) (and it may also be noted that the cap may be provided with rearwardly extending portions which additionally directly engage the cartridge carrier (50) to provide a more secure tension in the forward position, it will be appreciated that this cap arrangement could also be used in the previous embodiments). As shown in FIG. 7b upon removal of the cap the syringe carrier (50) and syringe (30) move rearwardly but it in this instance the rearward end of the cartridge (30) is short of the forward end of the drive element (13). Only upon the relative forward movement of the rear housing (24) toward the forward housing (22) does the drive element (12)

come into contact with the syringe (30) so as to compress the slideable member (12a) and trigger the compression switch (48d) so as to provide an injection ready indication.

FIG. 8 illustrates a possible optional additional feature in which the switches may further be used to provide a battery power function. In this function the housing portion (22) and (24) have been removed and the microprocessor of the indication module is able to identify this since contacts (48a and 48b) are closed whereas contacts (48d and 48c) are both open. The user may manually compress the front of the plunger (12) such that (12a) is moved rearwardly and compression switch (48d) is triggered. The microprocessor may recognise this as a battery test and provide a battery power signal dependent on the status of the battery.

FIG. 10 illustrates a drive element (112) for use in embodiments of the invention. As in the preceding embodiments the drive element (112) includes a self-contained indicator module (140) which only requires activation switches (148a, 148b) to interact with the housing (20) of the injection device (1) (such that the injection device does not require any other electrical components).

Figure 10A:
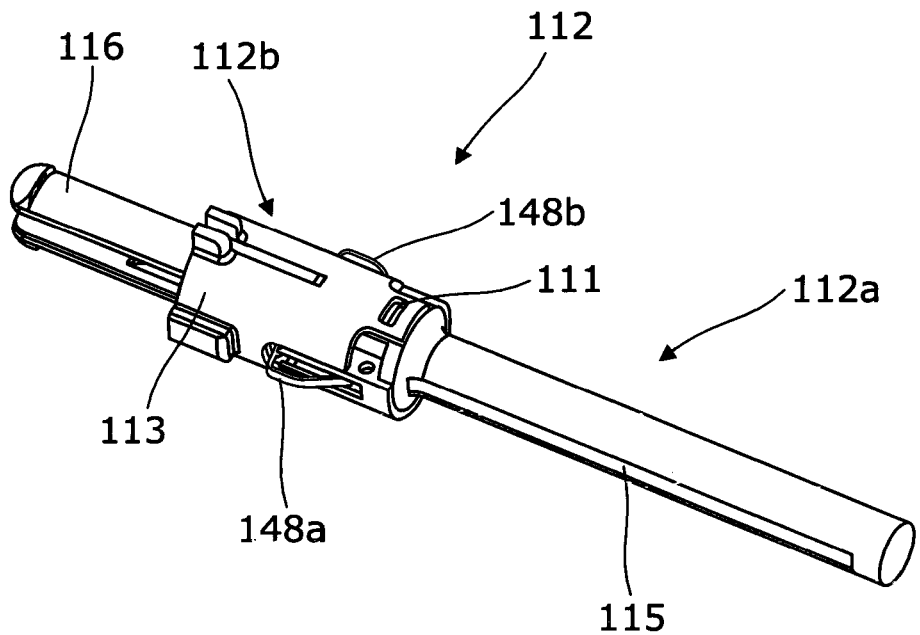
FIG. 10 is a series of three dimensional views of a drive element for use in embodiments of the invention.
Figure 10B:
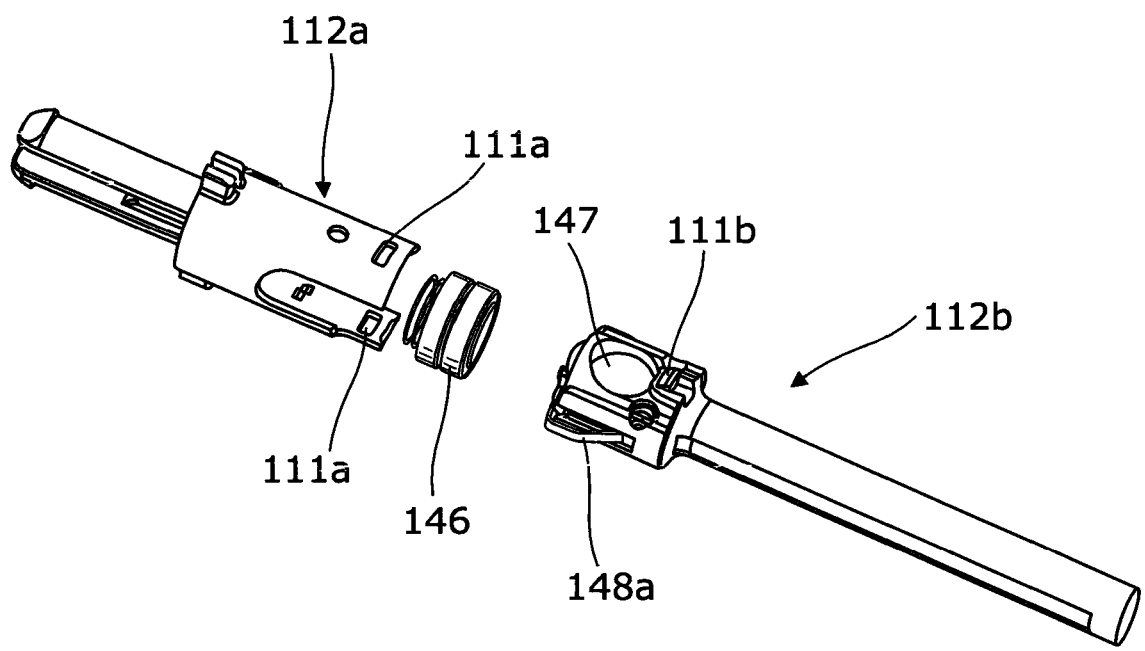

The drive element (112) of this embodiment comprises front (112a) and rear (112b) portions which are separable between an assembled configuration shown in FIG. 10(A) and a disconnected configuration shown in FIG. 10(B). The portions (112a and 112b) are connected together by a snap fit arrangement (111). The rear portion of the drive element (112a) includes the latch (116) and an outer body defining the portion of the drive element having an increased radial dimension (113). The forward portion of the drive element (112b) includes the elongate plunger section having a translucent portion (115) which forms a light transmitting member during use. The rearward end of the forward portion (112b) is configured to provide a supporting body for the components of the indicator module (140). In the assembled configuration, this supporting body is received within the portion of the drive element having an increased radial dimension (113). Both the forward (112b) and rearward portions (112a) are provided with suitable cut-outs (or apertures), which align in the assembled arrangement, through which the switches (148a and 148b) may extend. A further cut-out (or aperture) may be provided associated with the audible indicator (147) to allow transmission of sound.

Batteries (146), which may for example be at least "button cell" type battery, are provided to power the indicator module (140) and are generally retained between the separable front (112a) and rear (112b) portions of the drive element (112). Thus, the battery(s) may be arranged to be replaceable by the user. The user may disengage the cooperating engagement features (11a and 11b) of the separable front (112a) and rear (112b) portions in order to access the battery compartment. The cooperating engagement features (111a and 111b) may be snap fit features. For example in the illustrated embodiment one of the front (112a) and rear (112b) portions of the drive element (112) includes a pair of opposed tabs (111b) and the other is provided with a corresponding pair of apertures (111a). Conveniently, the rear portion of the drive element (112a) may remain in situ within the rearward housing portion (24) of the injection device (1) when the front portion (112b) is removed to enable replacement of the batteries (146).

Figure 10C:
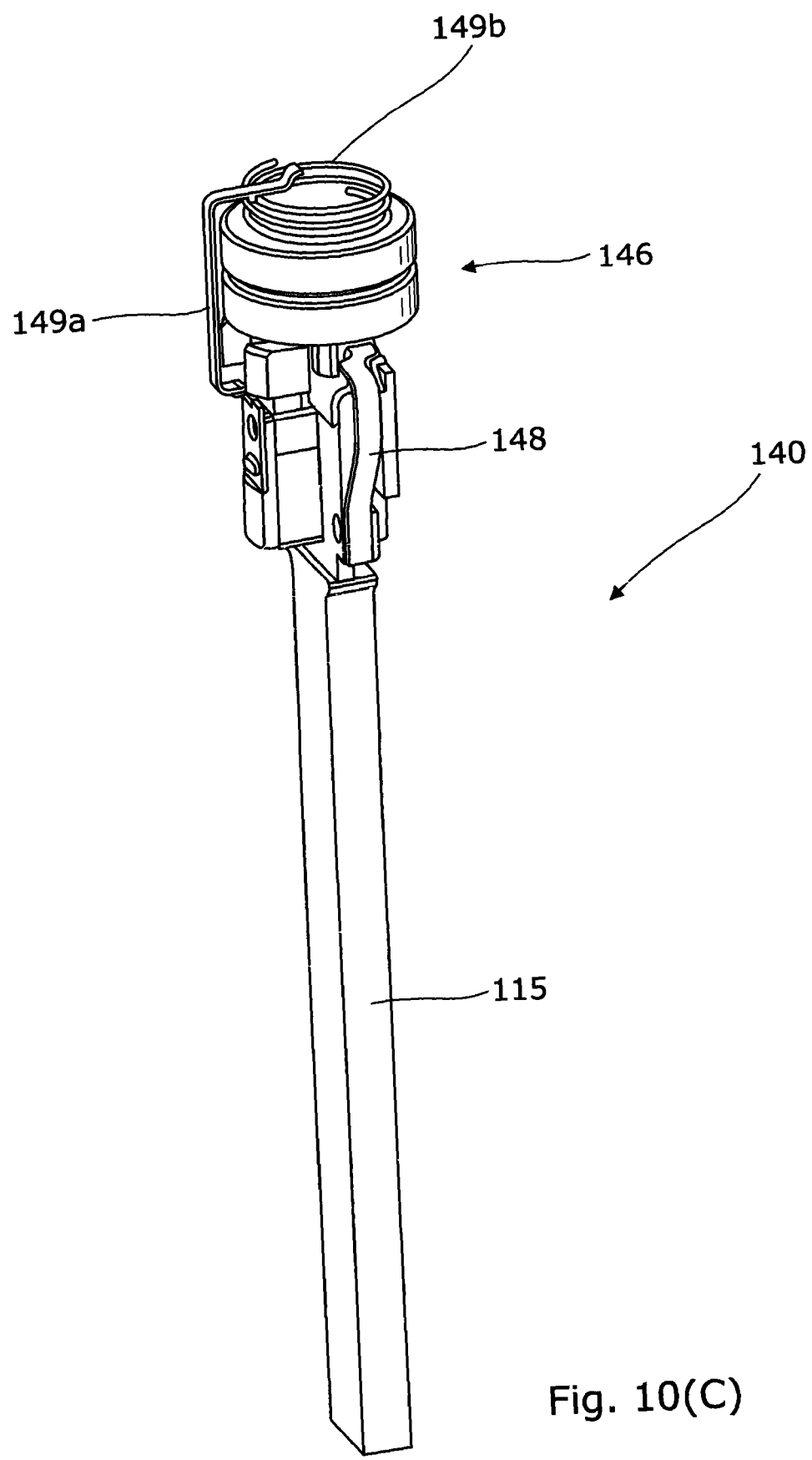

FIG. 10(C) shows the indicator module (140) without the body portions of the drive element (112). The batteries (146) are retained at the rearward end of the indicator module (140) by a retaining/contacting member (149a) and a retaining/contact spring (149b). It will be noted that the translucent portion (115) of this embodiment is formed separately from the forward body (112b) but integrally with the indicator module (140). This provides a convenient arrangement in which the translucent portion (115) is inserted into an inner bore of the forward body (112b) and aligns with a corresponding cut out of viewing window (as can be seen in FIG. 10(D)).

Figure 10D:
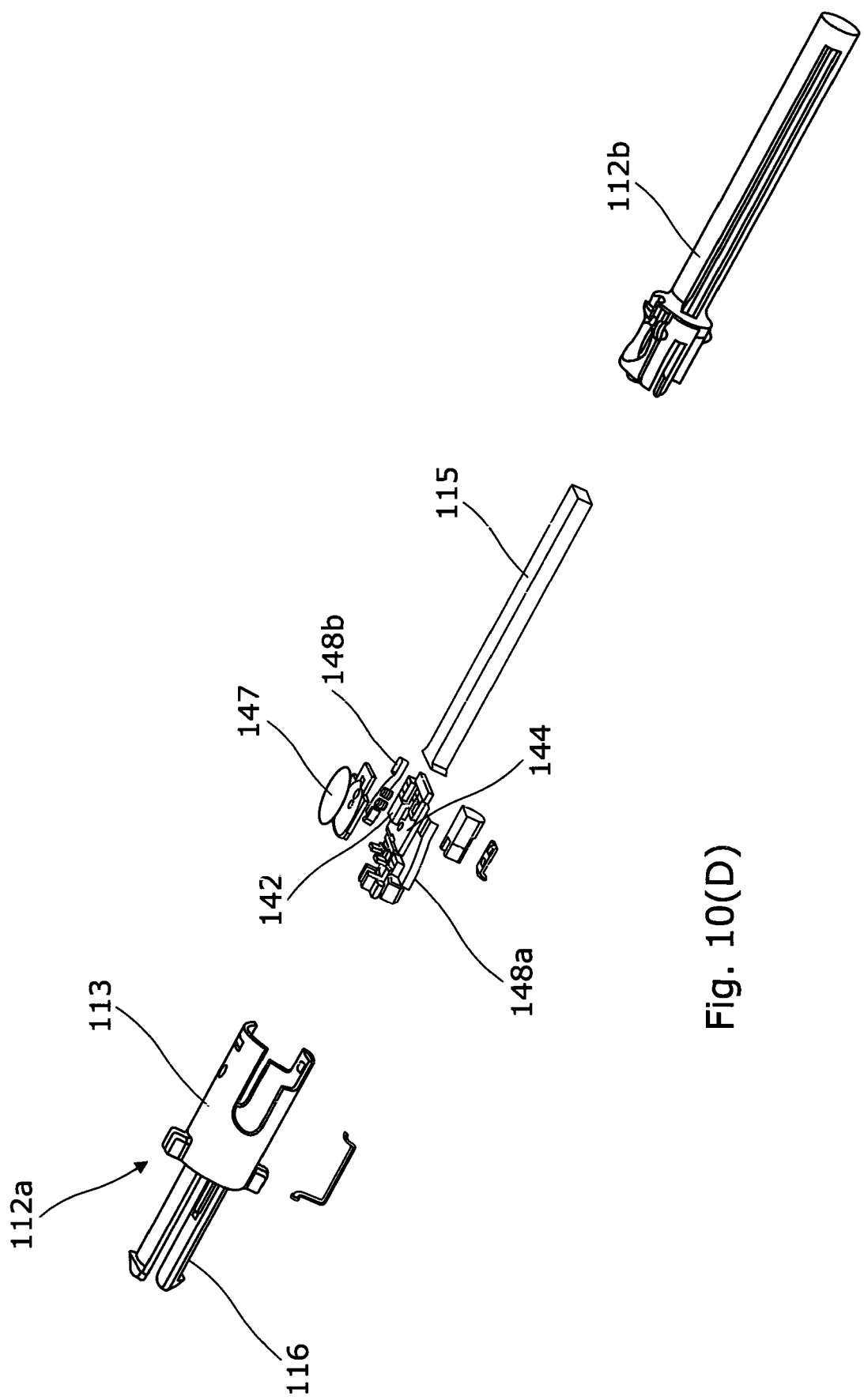

The arrangement of this embodiment can be seen in further detail in the exploded view of FIG. 10(D), in which the batteries (146) have been omitted. In particular, it can be seen that the indicator module (140) has essentially the same basic components as the earlier embodiments and includes a microprocessor (142), a printed circuit board (144) and a sound emitter (147). The sound emitter (147) is in the form of a piezoelectric transducer (which may also be referred to as a piezoelectric buzzer) which provides a conveniently compact and simple construction. In this embodiment the illumination device is integrally formed with the translucent section (115) of the drive element (112) (although it will be appreciated that these could alternatively be distinct components) and may, for example, comprise at least one embedded LED. Although the invention has been described above with reference to a preferred embodiment, it will be appreciated that various changes or modifications may be made without departing from the scope of the invention as defined in the appended claims.

For example, the signals from the switches may be utilised by the microprocessor to count the doses administered by the injection device. This may for example be useful where the device is intended to dispense a number of discrete (and possibly variable volume) doses from a single cartridge. In such an arrangement a display may be provided (for example an LCD or e-paper display) on the housing.

Whilst in the embodiment above the indication device comprises at least one LED and a loudspeaker, the skilled person will appreciate that other indication device may be suitable for use in embodiments of the invention. For example, alternative sound emitters such as a sounder, a buzzer (for example a piezoelectric-buzzer) may be used in place of a loudspeaker. Additionally, the indication device could for example comprise an eccentric motor which may, for example, provide a sound and/or tactile indication. Other forms of light emitters may be used, such as photoelectric devices, may be used as an alternative illumination device in place of the at least one LED.

Figure 11A:
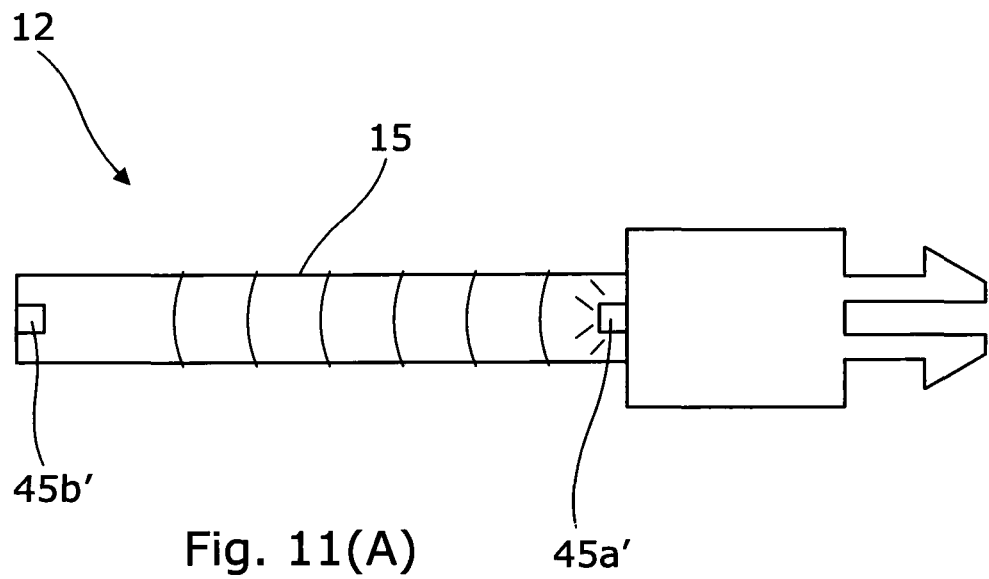
FIG. 11 is a schematic representation of a drive element using multiple illumination devices for use in embodiments of the invention.
Figure 11B:
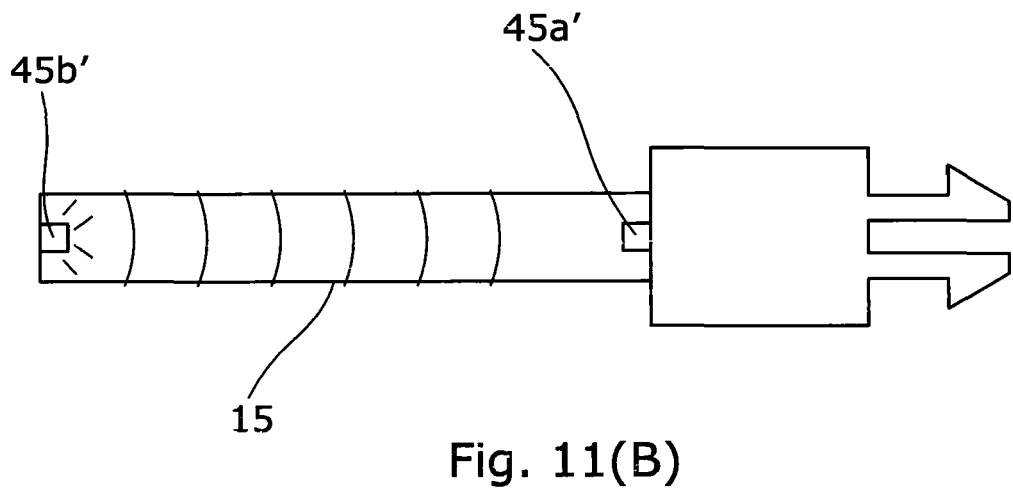
Figure 11C:
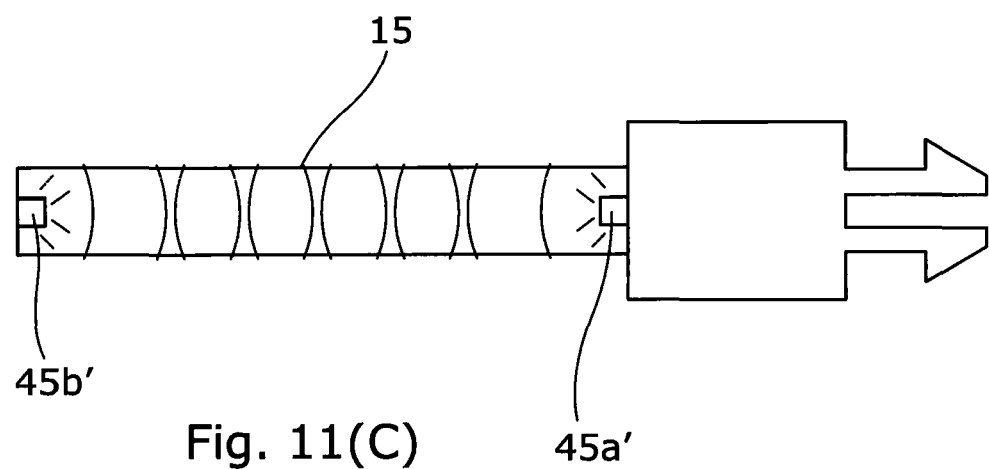

In embodiments including multiple illumination devices for use as indicators (such as that described above with reference to FIG. 5), at least two of the illumination devices (which may for example be LED's) may be provided at spaced apart locations. In particular the illumination devices could be in an opposed arrangement. For example, as shown in FIG. 11, one LED (45a') may be provided at the rearward end of the translucent portion (15) of the drive element (12) and another (45b') may be provided at a forward end of the translucent portion (15). This enables further visual indication effects to be generated as shown schematically in FIG. 11 (where the curved lines are provided to represent illumination from one of the devices): in FIG. 11(A) only the rearward LED (45a') is illuminating the translucent portion (15); in FIG. 11(B) only the forward LED (45b') is illuminating the translucent portion (15); and in FIG. 11(C) both the rearward LED (45a') and forward LED (45b') are illuminating the translucent portion (15). The rearward LED (45a') and forward LED (45b') may be different colours and therefore a blending effect may be provided when both LED's are illuminated. The blending effect may be tailored depending upon the colour and light intensity of the illumination from the light indicators.

The invention claimed is:

1. An injection device, comprising:
a housing for receiving a cartridge of medicament in use, the cartridge having a moveable piston for urging medicament from an interior of the cartridge, the housing including a radially inwardly projecting trigger point on an inside surface thereof;
a delivery mechanism for dispensing medicament from the cartridge, the delivery mechanism comprising:
a plunger configured to engage the piston of the cartridge, wherein the plunger is moveable from a first position to a second position during activation of the delivery mechanism to move the piston of the cartridge and expel a dose from said cartridge,
and wherein the plunger comprises:
a support body defined by a portion of the plunger and moveable with the plunger from the first position to the second position; and
an electrically-operated indicator module configured to generate an indication corresponding to the stage of use of the device based on an interaction with the trigger point, the indicator module being mounted to the support body and the indicator module comprising at least a battery, an indication device and a controller.

2. The injection device of claim 1, wherein the indicator module further comprises a switch which interacts with the trigger point to generate the indication corresponding to the stage of use of the device.

3. A drive element for an injection device, comprising:
a forward portion extending in a generally axial direction and configured for engaging a cartridge of medicament to expel a dose of medicament from the cartridge;
a rearward portion extending from the forward portion, the rearward portion defining a compartment and containing an indicator module, the indicator module comprising at least a battery, an indication device and a controller; and
a latch element arranged on a rearward end of the rearward portion for being releasably held in use by a corresponding latch element on the injection device.

4. The drive element of claim 3, wherein the drive element comprises separable body portions to allow access to the battery.

5. An injection device, comprising:
a housing for receiving a cartridge of medicament in use; and
a drive element moveable from a first position to a second position to expel a dose from the cartridge, and wherein the drive element comprises an electrically-operated indicator module having electrically conductive components for generating an indication corresponding to the stage of use of the device, and all of the electrically conductive components are disposed on or contained within the drive element.

6. The injection device of claim 5, wherein the indicator module includes a battery, an indication device, and a controller.

7. The injection device of claim 6, wherein the indicator device comprises at least one illumination device.

8. The injection device of claim 7 further comprising a translucent body extending along at least a portion of the drive element and arranged to transmit indications from the illumination device.

9. The injection device of claim 8, wherein the translucent body may be arranged to transmit illumination signals from the illumination device to a viewing window in the housing.

10. The injection device of claim 5, wherein the drive element further comprises at least one switch and the housing comprises at least one associated radially inwardly projecting trigger point arranged to engage the switch when the switch is in axial alignment with the trigger point.

11. The injection device of claim 10, wherein the trigger point comprises an axially extending rib.

12. The injection device of claim 10, wherein the drive element comprises a plurality of switches and the housing comprises a plurality of associated trigger points each disposed at a different axial location.

13. The injection device of claim 12, wherein each of the plurality of switches and associated trigger points are radially distributed about the housing and drive element.

14. The injection device of claim 5, wherein the drive element further comprises at least one switch and the housing includes at least one feature which is arranged to trigger the switch in a pre-determined pattern or periodic manner during axial movement of the drive element.

15. The injection device of claim 12, wherein each switch comprises an outwardly biased contact member which is deflected inwardly by the associated trigger point.

16. The injection device of claim 5, wherein the housing comprises a shroud assembly arranged to shroud the needle of the cartridge after use, and wherein the drive element further comprises a switch which is arranged to engaged a portion of the shroud when the drive element is in a forward position.

17. The injection device of claim 5, wherein the drive element further comprises a compression switch, which is activated by compressive load on the drive element.

18. The injection device of claim 17, wherein the device further comprises a removable needle shield and wherein removal of the needle shield is arranged to compress the drive element.

19. The injection device of claim 18, wherein the cartridge is held against a rearward biasing force by the needle shield and moves rearwardly against the drive element upon removal of the needle shield.

20. The injection device of claim 17, wherein the housing comprises front and rear portions which are relatively axially slidable and wherein axial compression of the housing portions is arranged to compress the drive element.

21. The injection device of claim 5, wherein the housing comprises front and rear separable portions to allow removal and replacement of the cartridge, and wherein upon separation of the housing portions the drive member is moved to a position in which the indicator is deactivated.

22. The injection device of claim 21, wherein in the separated position, a switch on the drive element may be used to test the battery power status of the indicator.

23. The injection device of claim 5, wherein the indicator module is arranged to provide a plurality of different color visual illuminations.

24. The injection device of claim 5, wherein the indication corresponding to the stage of use of the device includes one or more of a ready to fire signal, an injection initiation signal, an injection complete signal, a device safe signal, or an alarm signal.

25. The injection device of claim 5,
wherein the injection module comprises a switch which is triggered by contact with a complementary feature when axial movement of the drive element relative to the housing aligns the feature and switch and wherein the feature is profiled along its axial length such that the switch is repeatedly activated during axial movement of the drive element.

26. The injection device of claim 25, wherein the feature comprises a sequence of radial projections at spaced apart axial locations.

27. The injection device of claim 25, wherein the feature has a periodic profile in the axial direction.

28. The injection device of claim 25, wherein the feature comprises a toothed track.

29. The injection device of claim 25, wherein the switch is provided on the drive element and the feature is formed on an inner surface of the housing.

30. The injection device of claim 25, wherein the injection device further comprises a controller, the controller being arranged to monitor the repeated activation of the switch to measure movement of the drive element.

* * * * *